(12) United States Patent
Zhang et al.

(10) Patent No.: US 8,385,998 B2
(45) Date of Patent: Feb. 26, 2013

(54) CONTACT LENS INTEGRATED WITH A BIOSENSOR FOR THE DETECTION OF GLUCOSE AND OTHER COMPONENTS IN TEARS

(76) Inventors: Jin Zhang, London (CA); William Gerald Hodge, London (CA)

( * ) Notice: Subject to any disclaimer, the term of this patent is extended or adjusted under 35 U.S.C. 154(b) by 435 days.

(21) Appl. No.: 12/588,733

(22) Filed: Oct. 26, 2009

(65) Prior Publication Data

US 2010/0113901 A1    May 6, 2010

Related U.S. Application Data

(60) Provisional application No. 61/193,055, filed on Oct. 24, 2008.

(51) Int. Cl.
*A61B 5/1455* (2006.01)
(52) U.S. Cl. ......................................... 600/319; 600/318
(58) Field of Classification Search ........... 600/309–344
See application file for complete search history.

(56) References Cited

U.S. PATENT DOCUMENTS

| | | | |
|---|---|---|---|
| 6,485,703 B1 | 11/2002 | Cote et al. | |
| 6,579,721 B1 * | 6/2003 | Natan et al. | 436/164 |
| 6,589,779 B1 | 7/2003 | McDevitt | |
| 6,602,702 B1 | 8/2003 | McDevitt et al. | |
| 6,681,127 B2 | 1/2004 | March | |
| 7,166,458 B2 | 1/2007 | Ballerstadt et al. | |
| 7,329,415 B2 | 2/2008 | Lally et al. | |
| 7,638,137 B2 * | 12/2009 | Chauhan et al. | 424/429 |
| 2003/0043341 A1 * | 3/2003 | Turner et al. | 351/160 R |
| 2004/0027536 A1 * | 2/2004 | Blum et al. | 351/168 |
| 2004/0078219 A1 * | 4/2004 | Kaylor et al. | 705/2 |
| 2004/0096477 A1 | 5/2004 | Chauhan et al. | |
| 2004/0241207 A1 | 12/2004 | Ghauhan et al. | |
| 2004/0258727 A1 * | 12/2004 | Liu et al. | 424/423 |
| 2006/0088449 A1 * | 4/2006 | Thorsen et al. | 422/100 |
| 2007/0105176 A1 | 5/2007 | Ibey et al. | |
| 2008/0063898 A1 | 3/2008 | Lally et al. | |

FOREIGN PATENT DOCUMENTS

| | | |
|---|---|---|
| WO | WO 02/03855 A1 | 1/2002 |
| WO | WO 2004/046726 A2 | 6/2004 |
| WO | WO 2004/080297 A1 | 9/2004 |

* cited by examiner

*Primary Examiner* — Eric Winakur
*Assistant Examiner* — Marjan Fardanesh
(74) *Attorney, Agent, or Firm* — Hill & Schumacher; Lynn C. Schumacher

(57) ABSTRACT

The present invention provides contact lens with integrated biosensor for the continuous, non-invasive monitoring of physiological glucose by employing biocompatible nano-structure-laden lens materials. These contact lenses can be worn by diabetics who can colorimetrically see changes in their contact lens color or other fluorescence-based properties, giving an indication of tear and blood glucose levels. This invention for the glucose biosensor based on the new disposal contact lens provides a safe, convenient and non-expensive glucose sensing device. The sensing device disclosed herein provides an efficient and noninvasive solution for monitoring blood glucose.

23 Claims, 11 Drawing Sheets

Top-down view

Cross-section view

CONTACT LENS INTEGRATED WITH A BIOSENSOR FOR THE DETECTION OF GLUCOSE AND OTHER COMPONENTS IN TEARS

RELATED PATENT APPLICATIONS

This patent application claims priority of the U.S. patent application No. 61/193,055 filed on Oct. 24, 2008, the whole content of which is incorporated herein by explicit reference for all intents and purposes.

FIELD OF THE INVENTION

The present invention relates to disposable contact lens biosensors for the continuous, non-invasive monitoring of physiological glucose by employing biocompatible nanostructure-laden lens materials. These nanocomposite-based contact lenses are able to be used as dug delivery device, for instance, delivery of artificial tears to diminish the symptoms of dry eyes. These contact lenses can be worn by diabetics who can colorimetrically see changes in their contact lens color or other measurable signals including fluorescence, and magnetorestrictive properties, giving an indication of tear and blood glucose levels.

BACKGROUND TO THE INVENTION

Blood is often used in clinic to trace certain constituents to diagnose related diseases. To get blood sample needs a invasive detection requiring arterial or venous puncture, by which means it normally brings a lot of side effects, and needs to be avoided. Therefore, other body fluids are alternative sources to be used for tracing the constituents as being symptomatic of the medical health of patients, including urine, saliva, and tear. It has been more and more interacting to trace the corresponding constituents from tear rather than blood because of its non-invasive test, safety and convenience. However, there are several challenges to measure constituents from tear. First it is hard to collect tear sample. Glass capillaries are normally used to collect test sample [1]. But, it may take at least 10 min to collect 10 µl of tear sample [2]. Secondly, the concentration of the constituents in tear is much lower than that in blood. Table I lists the detectable constituents in tears for the diagnosis of the related disease. This invention is related to continuously detect the glucose and other constituencies in tear through a disposable, nanostructured sensor integrated with contact lens. Below describes the major constituents in tear which can be detected through this invention.

Diabetes mellitus is a chronic systemic disease characterized by disorders in both the metabolism of insulin, carbohydrate, fat and protein and the structure and function of blood vessels [3]. As is known, glucose is the main circulating carbohydrate in the body. In normal individuals, the concentration of glucose in blood is tightly regulated, usually in the range between 80 and 120 mg/100 ml, during the first hour or so following a meal. The hormone insulin, normally produced by the beta cells in the pancreas, promotes glucose transport into skeletal muscle and adipose tissue as well as promoting uptake of glucose by the liver for storage as glycogen [3].

In diabetes mellitus, insulin production and/or uptake is compromised and, consequently, blood glucose can be elevated to abnormal concentrations ranging from 300 to 700 mg/100 ml. Over time, elevated blood glucose can cause serious damage to the body. Diabetes can result in circulatory problems which may lead to kidney failure, heart disease, gangrene and blindness. Diabetes is one of the most significant causes of death in Canada due to diabetic complications and the rapid development of arteriosclerosis in inadequately treated diabetic patients [3].

Accurate determination of glucose levels in body fluids, such as blood, urine, and cerebro-spinal fluid, is a major aid in diagnosing and improving the therapeutic treatment of diabetes. It can reduce the long-term risk for developing coronary artery disease, visual impairment, renal failure, and peripheral vascular disease. The most widespread example of a commercial biosensor is the blood glucose biosensor. A biosensor is a compact analytical device, which converts a biologically induced recognition event into a usable signal [4]. A biosensor includes three (3) parts: (1) the sensitive biological element (biological material, or a biologically derived material or biomimic); (2) the transducer or the detector element) that transforms the signal resulting from the interaction of a target analyte with the biological element into another signal (works in a physicochemical way; optical, piezoelectric, electrochemical, etc.) that can be more easily measured and quantified; (3) the signal processors that is primarily responsible for the display of the results in a user-friendly way.

In hospitals, there is a continual need for medical biosensor based devices that are used for real-time Point-of-Care Testing. Furthermore, recent advances in insulin pump technology have created a demand for concurrent advances in the area of glucose sensing. Currently, commercial blood glucose sensors available for diabetics are chemical sensors based on the enzyme glucose oxidase which breaks down glucose in the presence of oxygen into hydrogen peroxide. The produced hydrogen peroxide reacts either electrically or optically with molecules, producing a change proportional to the amount of glucose within the blood volume.

These biosensors however have the disadvantage of requiring that blood be drawn from the patient through either a forearm or finger prick, such as the Precision Q-I-D and the Glucometer Elite XL. To date, millions of diabetics prick their fingers for a drop of blood a few times a day to check glucose levels. Besides being uncomfortable, these tests can miss sudden dips or spikes in blood sugar. Frequent readings are easier with sensors that can be implanted in a patient's skin. But the glucose sensors available today can cause infections after a few days, and they are bulky and expensive.

In recent years, a few devices have been introduced that allow users to test their glucose levels by drawing blood from their arm instead of the tips of their fingers, such as implantable enzymatic sensors, such as the Medtronic-MiniMed CGMS. This type of device requires an even higher degree of biocompatibility because of the risk of thrombosis or embolism. These cutting edge intravenous sensors exhibit lag times of less than three minutes as well as impressive in vivo stability. However, the major obstacle to the use of enzymatic glucose sensing is a phenomenon known as membrane biofouling, which is the clogging of the selective membrane by other molecules present in the blood stream or interstitial spaces.

Although many methods of measuring blood sugar levels have been investigated [5-11], the inconvenience of blood sugar monitoring has not fundamentally improved in recent years. For this reason, there is clearly a need for the development of non-invasive and continuous method of blood sugar monitoring, which is readily available and simple to perform on a daily basis for a reasonable cost. Generally, continuous glucose level monitoring does not measure blood glucose directly, but relies instead on measurement of the glucose levels in other biological fluids.

Tear fluid is more accessible than blood or interstitial fluid and more continuously obtainable and less susceptible to dilution than urine. The study on the correlation of tear glucose and blood glucose has been reported since 1980's [12]. Diabetic and nondiabetic tear glucose mean values were 0.35±0.04 mmol/L and 0.16±0.03 mmol/L, respectively [13-16].

United States Patents: 20070105176A1 and U.S. Pat. No. 7,166,458 are related to use the implantable artificial lens to monitor the tear/blood glucose level. However, implanted lens device always produce serious side-effect. As other implantable blood glucose sensors, these intravenous sensors require an even higher degree of biocompatibility because of the risk of thrombosis or embolism. Therefore, the present invention is directed to a non-invasive, continuous biosensor (e.g. glucose) which is realized through nanostructure-loaded contact lens. For the case of glucose sensors, the market size has been studied with over $7 billion in 2004. The need in the market is particularly related to the non-invasive and continuous sensors.

The use of glucose sensing contact lenses is a new paradigm in glucose monitoring. The idea of lens sensor devices is to not only correct vision, but to continuously monitor the level of glucose in tears non-invasively as well. A sensing contact lens would sample analytes in the tear fluid located on the surface of the eye. The sensor is preferably relatively inexpensive, mass producible, non-toxic and able to survive sterilization by autoclaving. It has been reported that tear glucose concentrations are related to blood glucose levels [5]. However, insulin concentrations in tears of subjects who were fasted for 12 hours were lower than those in tears of subjects who were fed tear glucose. Thus, it is a challenge to monitor tear glucose at lower concentrations. Furthermore, the current means of detection suffers from the design of the sample collector, suitable bioprocess probing, and the contact lens matrix (contact lens is normally made by hydrogels). To wear contact lens for one week requires that the contact lens needs to be produced with materials with high oxygen permeability.

Various contact lens sensors have been proposed to track tear glucose levels. For instance, WO04046726A2 discloses use of "vesicles" in a surface coating on the contact lenses to entrap the FITC-dextran/TRITC-Con A assay components. TRITC-Con A-FITC has also been disclosed in different patents as an example, such as U.S. Pat. Nos. 6,485,703, and 6,602,702.

However, there are several hurdles to over come to obtain a feasible contact lens sensor, these hurdles relate to the low concentration of tear samples or analyte, non-continuous monitoring, and vision influence. Moreover, most systems proposed use polymer materials (lens materials) as the analyte collector. Unfortunately, these polymer materials are prone to changes in structure depending on pH or temperature. Furthermore, the patents of Novartis AG mention the vesicle, e.g. a nanocapsule having a multilayered shell of polyelectrolytes, which are soft materials, are biodegradable, and lose protein (Con A) in the body. This is a major safety issue.

U.S. Pat. No. 6,681,127 and WO04080297A1 disclose use of a surface coating on contact lenses to entrap glucose assay components.

U.S. Pat. No. 7,329,415 and United States Patent Publication No. 20080063898A1 disclose that a vesicle can include "a nanocapsule having a multilayered shell of polyelectrolytes". These documents disclose liposome nano-encapsuls in contact lens which are not readily used for glucose monitoring due to the fact they are soft materials which cannot keep a stable shape for long periods of time so that they cannot be used for continuous monitoring.

WO0203855A1 discloses a contact lens where an assay is incorporated "within a discrete zone or spot" or "in a strip on the periphery of the device".

U.S. Pat. No. 6,485,703 disclose beads to be injected into the skin for glucose monitoring. These beads carry the FITC-dextran/TRITC-Con A assay components. This is not an contact lens device but it is one example of using FITC-dextran/TRITC-Con A to detect glucose.

United States Patent Publication No. 20070105176A1 discloses an implantable system which is a functionalized nanoparticle.

U.S. Pat. No. 7,166,458 discloses an implantable device, utilizing "beads or particles" embedded in a macroporous matrix. United States Patent Publication Nos. 20040241207A1 and 20040096477A1 disclose a contact lens fabricated for drug delivery by nanoencapsulation of a drug within nanocapsules dispersed within the contact lens, so that the drug can diffuse out into the tear film on the eye. Nanocapsules could include silica nanospheres, or gelatin, or sodium alginate nanoparticles.

U.S. Pat. No. 6,589,779 and U.S. Pat. No. 6,602,702 disclose an in vitro system for analyte detection using chemically sensitive particles and FRET signaling. These particles are composed of polymeric resin with fluorescent indicator and quencher chemically coupled to them. The particles are from 0.05-500 microns in diameter.

It would therefore be advantageous to provide a contact lens having incorporated therein a biosensor for monitoring glucose levels in tears.

SUMMARY OF THE INVENTION

The present invention provides contact lens biosensor for the continuous, non-invasive monitoring of physiological glucose and other bioanalyte constituents in tears by employing biocompatible nanostructure-laden lens materials. These contact lenses can be worn by diabetics who can colorimetrically see changes in their contact lens color or other fluorescence-based properties, giving an indication of tear and blood glucose levels.

This invention for the glucose biosensor integrated with a disposable contact lens provides a safe, convenient and non-expensive glucose sensing device. The biosensor sensing device disclosed herein provides an efficient and non-invasive solution for monitoring blood glucose.

The present invention provides a contact lens with integrated biosensor, comprising:
  a) a contact lens having incorporated therein a biosensor for sensing bioanalytes present in tears;
  b) the biosensor including a physiologically compatible oxygen permeable substantially transparent and flexible substrate, and physiologically compatible porous nanostructures adhered on said physiologically compatible oxygen permeable and flexible substrate, a physiologically compatible fluorescent assay containing at least one physiologically compatible fluorescent dye encapsulated in said physiologically compatible porous nanostructures, said physiologically compatible fluorescent dye being selected to react or bind with a selected bioanalyte present in tears such that reacting or binding of the bioanalyte with the physiologically compatible fluorescent dye is responsively accompanied by a detectable change in optical properties of the physiologically compatible fluorescent dye indicative of the presence of the bioanalyte in tears when the contact lenses with integrated biosensor is on a person's eye; and c) said biosensor being located in said contact lens at a position off centre in the contact lens such as to not directly obstruct the vision of the person wearing the contact lens.

The present invention also provides a method of producing a contact lens with integrated biosensor, comprising the steps of:

a) producing a biosensor by i) preparing silica nanoparticles with encapsulated organic dye by mixing a silane precursor, TEOS, and an organic dye in absolute alcohol whereby the following reactions take place

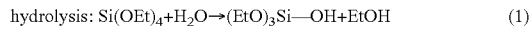

hydrolysis: $Si(OEt)_4 + H_2O \rightarrow (EtO)_3Si-OH + EtOH$ (1)

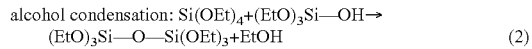

alcohol condensation: $Si(OEt)_4 + (EtO)_3Si-OH \rightarrow (EtO)_3Si-O-Si(OEt)_3 + EtOH$ (2)

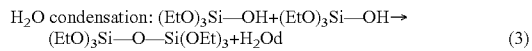

$H_2O$ condensation: $(EtO)_3Si-OH + (EtO)_3Si-OH \rightarrow (EtO)_3Si-O-Si(OEt)_3 + H_2Od$ (3)

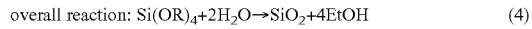

overall reaction: $Si(OR)_4 + 2H_2O \rightarrow SiO_2 + 4EtOH$ (4)

encapsulaed organic dye is trapped in polymerized silica nanoparticles by ionic interaction;

ii) assembling dye-loaded silica nanoparticles onto a surface of a physiologically oxygen permeable substrate and adhering them thereto to form one or more layers;

b) fabricating a contact lens and integrating the biosensor into the contact lens with the biosensor being located in said contact lens at a position off centre in the contact lens such as to not directly obstruct the vision of the person wearing the contact lens.

It will be appreciated that this is only one of many was of producing a contact lense with integrated biosensor, and the method is not restricted to silica nanoparticles.

An alternative way of encapsulation of fluorophore assays in porous nanostructures is water-in-oil microemulsion. A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

Table 1 lists the detectable constituents in tears for the diagnosis of the related disease

The organic dye A, TRITC-dextran is red color, and organic dye B, FITC, is green in the florescent microscopy.

Figure 9:
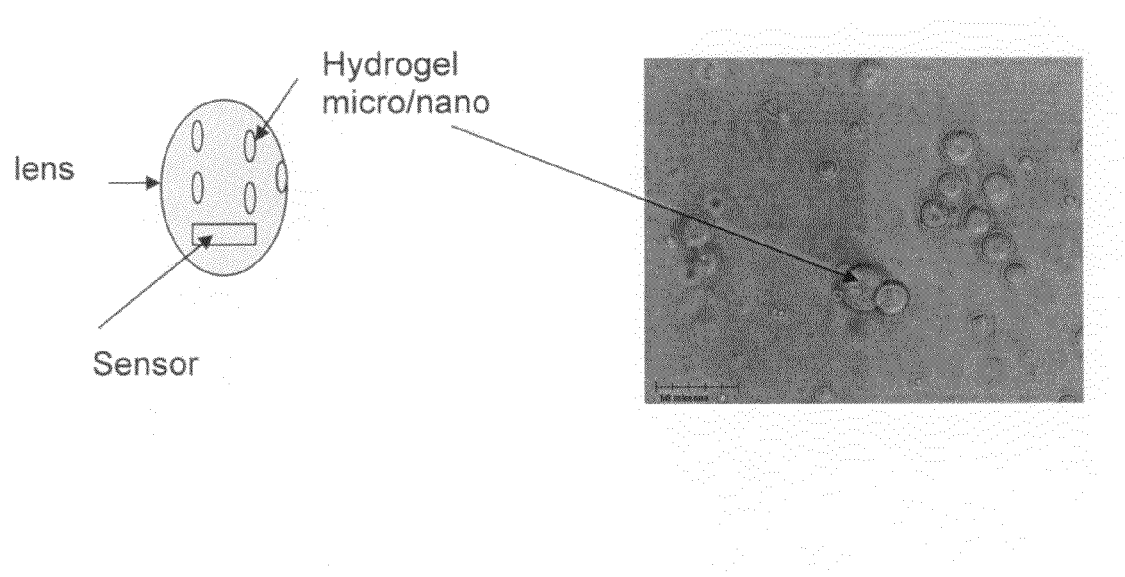

FIG. 9 shows the contact lens is able to load micro/nanospheres to deliver artificial tears or other payload to diminish the symptoms of dry eyes which is the key challenge to contact lens.

Figure 10:
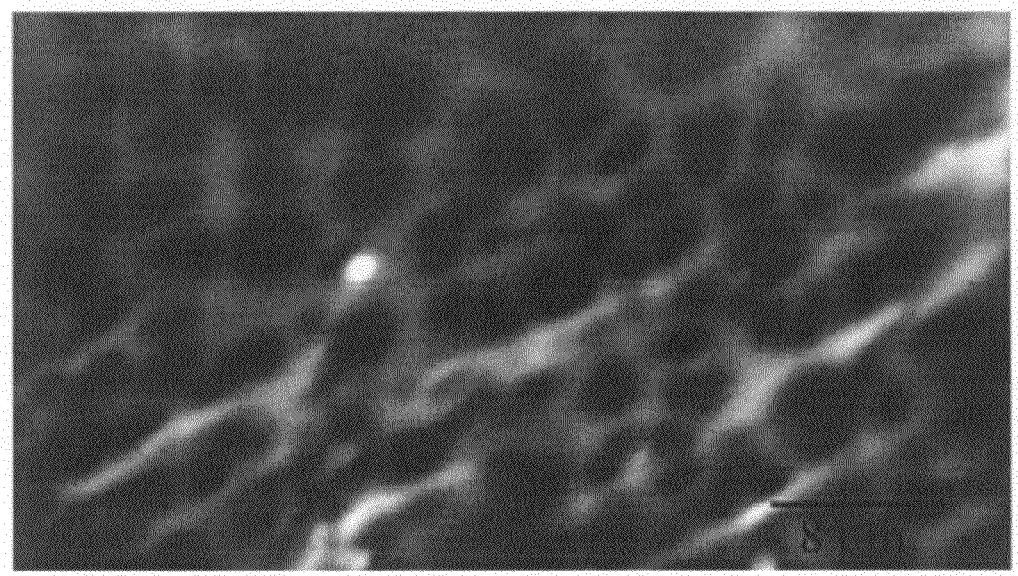

FIG. 10 displays the porous hydrogels len materials, e.g. p(HEMA), which has high oxygen permeability to help minimize the symptoms of dry eyes. Meanwhile, the porous structure helps the laden sensor absorb tear sample.

Figure 11:
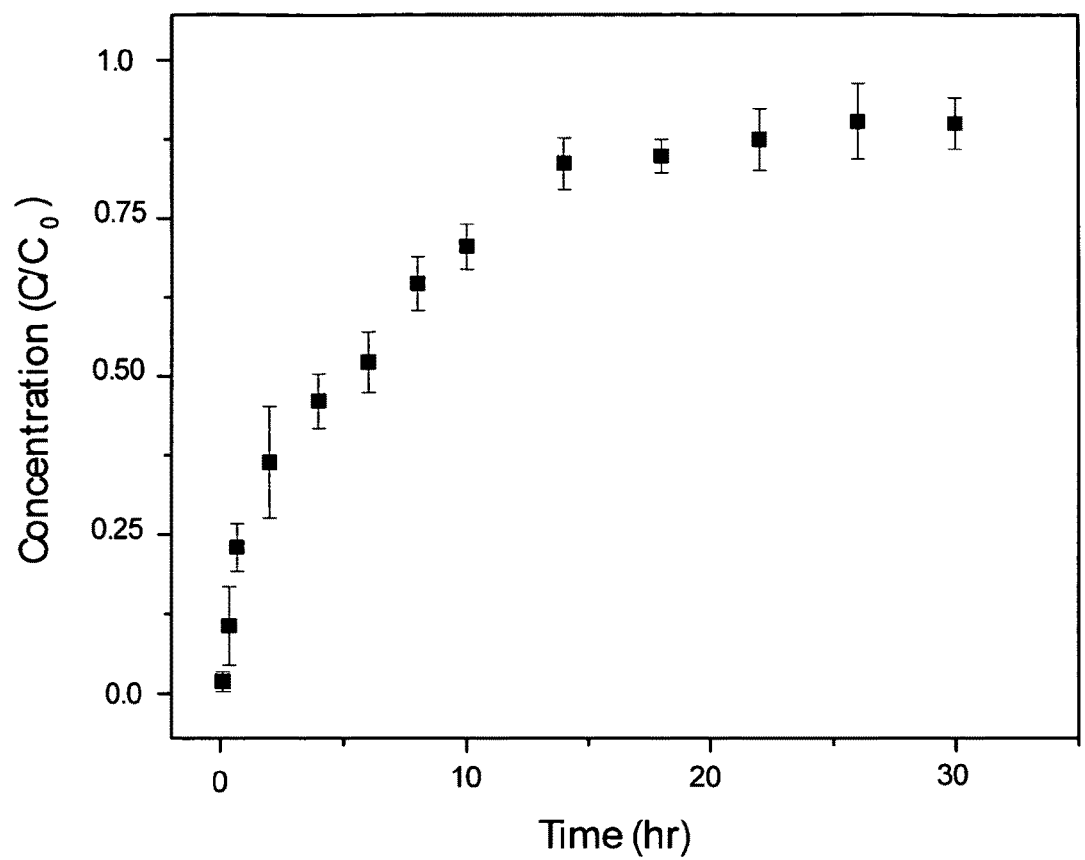

FIG. 11 shows a releasing profile of artificial tears through the micro/nano sphere-loaded contact lens sensor.

DETAILED DESCRIPTION OF THE INVENTION

Generally speaking, the embodiments described herein are directed to disposable contact lens biosensors for the continuous, non-invasive monitoring of bioanalytes including, but not limited to, physiological glucose. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, disposable contact lens biosensors for the continuous, non-invasive monitoring of bioanalytes are disclosed herein.

As used herein, the terms "about", and "approximately" when used in conjunction with ranges of dimensions, concentrations, temperatures or other physical or chemical properties or characteristics is meant to cover slight variations that may exist in the upper and lower limits of the ranges of properties/characteristics.

There are three major reasons that make porous nanostructures ideal materials as optical probes. Firstly, most nanostructures exhibit stable optical signals, porous nanostructures, acting as nanocontainners, can keep the organic dye/proteins stable because most of organic dye and proteins decompose or in-active easily. In addition, due to large surface area and porous structure, nanostructures can act as an analyte, e.g. glucose, glucose oxidase (GOx), reservoir which is helpful for uniform immobilization and high loading of analyte, glucose, GOx, for glucose sensing. Thirdly, the large surface areas of nanostructures may lead to higher selectivity for glucose sensing.

In addition, the porous nanostructures are able to keep multiple dyes and materials to the same sensing medium, allowing synergistic sensing schemes for the detection of more types of analytes, based on ion correlation or enzyme reaction.

Figure 1:
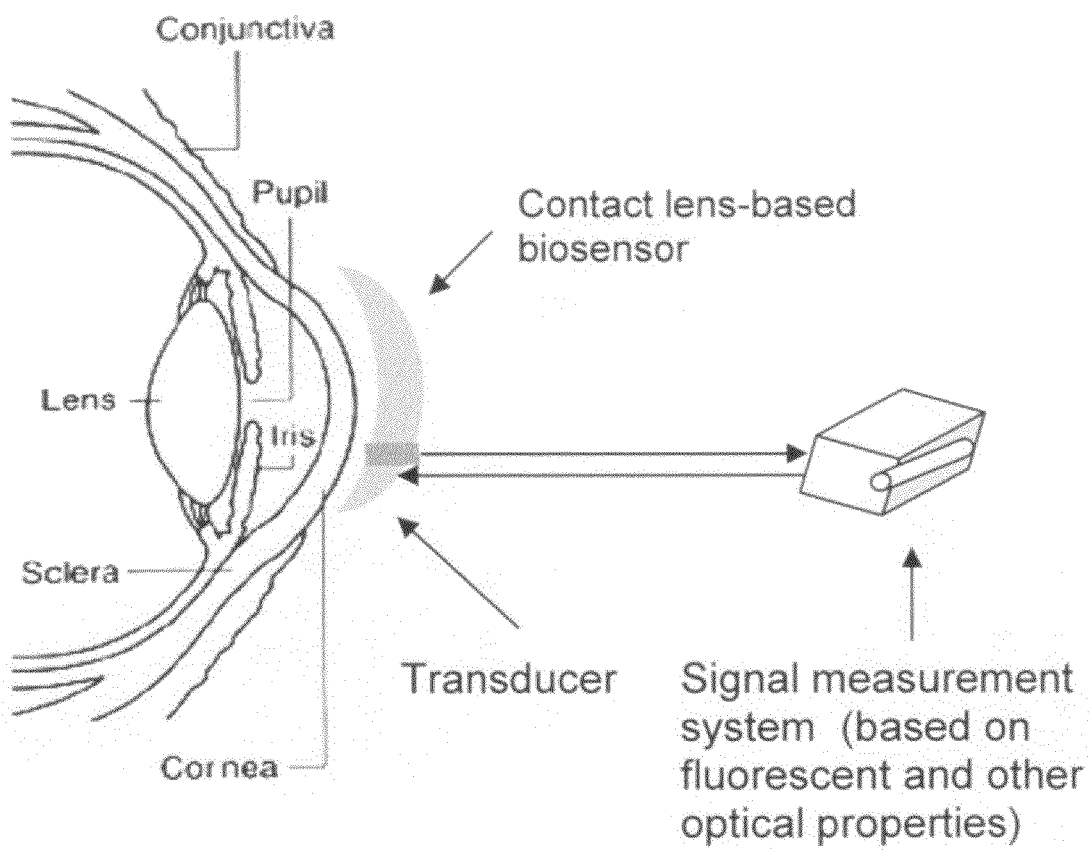
FIG. 1 shows a cross view of an eye with a nanostructure-laden contact lens biosensor in accordance with the present invention.
Figure 2:
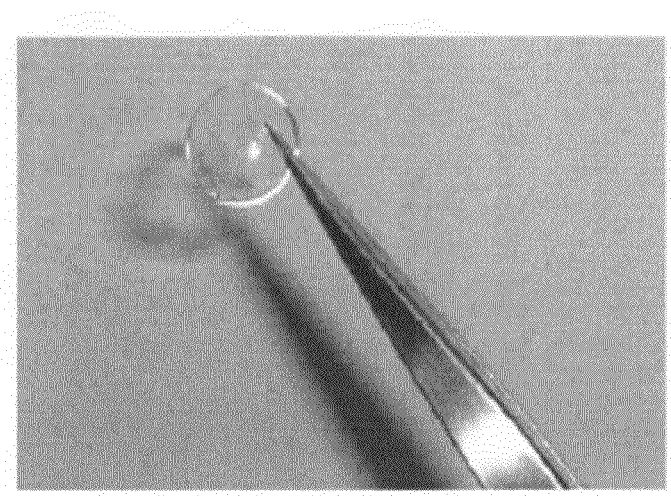
FIG. 2 is the photo of the invented optical sensor integrated into a contact lens. It also provides an illustration showing a top-down view and a cross-section view along with dimensions of the contact lens device.
Figure 2:
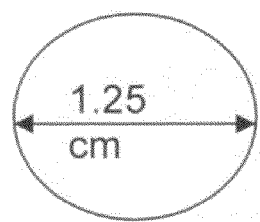
Figure 2:

FIG. 1 shows the illustration of using the contact lense with integrated sensor for the continuous, non-invasive detection of bioanalyte constituents in tears. FIG. 2 shows a photo of the contact lense, and a top-view and a cross view of an eye with a nanostructure-laden contact lens biosensor in accordance with the present invention.

The present invention generally utilizes sensing the interaction between a fluorophor-binding protein and an analyte of interest in tears, of which glucose is but one example. An example of an organic dye used in the present invention for detection of glucose is FITC Dextran-TRITC-Con. The basic transduction principle is changing resonance energy transfer (RET) efficiency from fluorescein isothiocyanate (FITC) to tetramethylrhodamine isothiocyanate (TRITC), as FITC-dextran is displaced from TRITC-Concanavalin A (Con A) with the addition of glucose. That is, there is a red shift which occurs as glucose binds. Thus, glucose concentration can be estimated from fluorescent resonant energy transfer (FRET) efficiency, and the ratiometric nature of the FRET analysis method allows variations in instrumental parameters, assay component concentrations, and measurement configuration to be internally compensated [17].

FITC Dextran (MW9 kDa, 150 kDa and 2 MDa) and Succinyl-Con A (MW 54 kDa) were purchased from Sigma-Aldrich. Aqueous stock solutions of 0.5 mg/mL and 1 mg/mL were prepared in dionized (DI) water for dextran and Con A, respectively, and the pH was adjusted to 8.5 by titrating with NaOH. Tetramethylrhodamine isothiocyanate (TRITC, Molecular Probes) was used to label succinyl-Con A using a standard amine-labelling protocol [17]. Glucose, from Sigma, was dissolved in DI water at neutral pH, to prepare a 100 mg/mL stock solution. All solutions used in the experiments involving Con A contained 1 mM concentrations of calcium chloride ($CaCl_2$) and magnesium chloride ($MgCl_2$) salts to preserve Con A and glucose binding. Finally, absorbance spectra were collected using a UV-Vis absorbance spectrometer.

Figure 3:
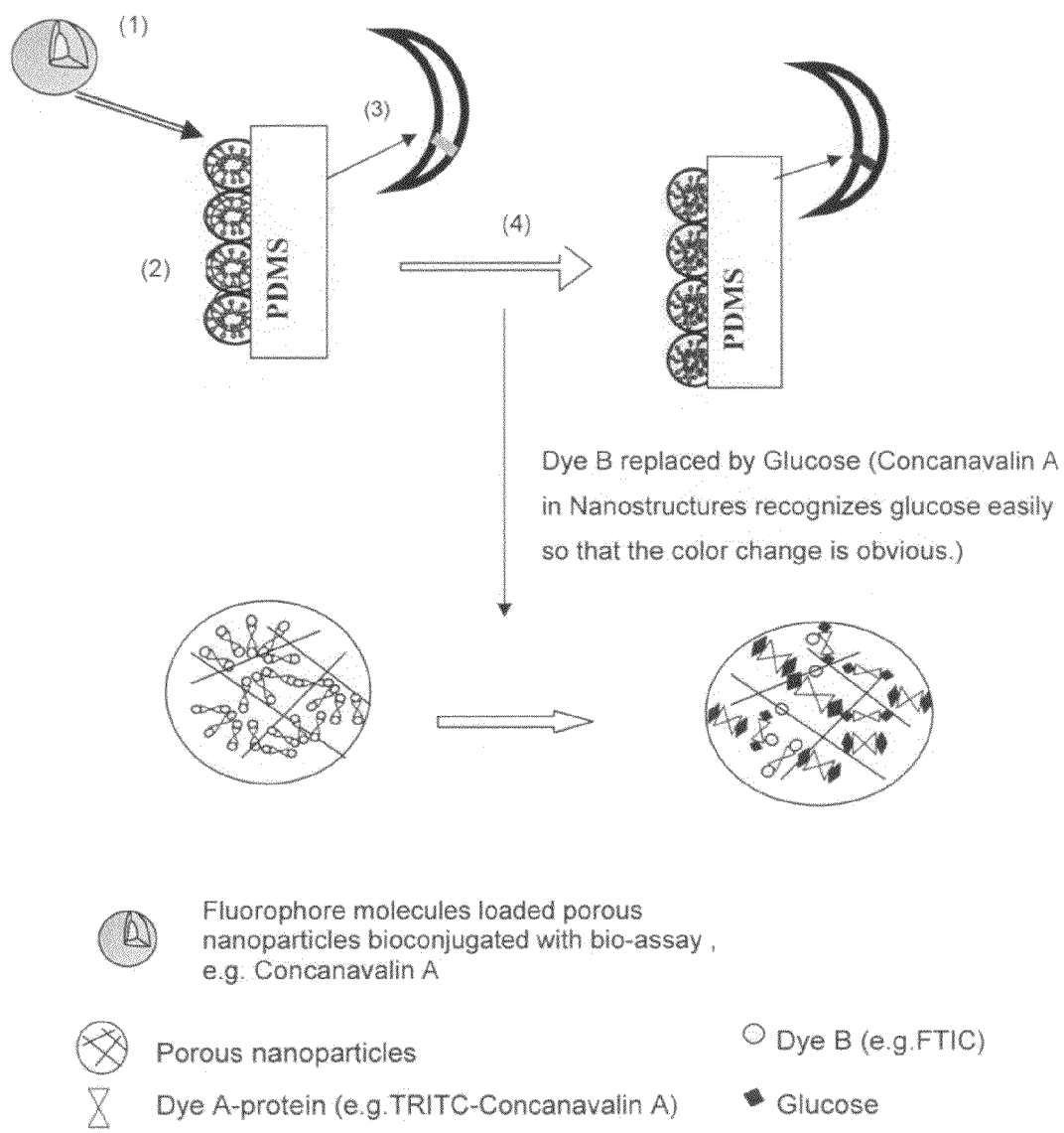
FIG. 3 is a diagrammatic illustration of the steps for producing the nanostructures-loaded contact lens biosensor in accordance with the present invention.

FIG. 3 illustrates an exemplary, non-limiting process for producing the nanostructures-loaded contact lens biosensor according to the present invention. In step (1) FITC Dextran-TRITC-Con A is encapsulated within silica nanoparticles. A modified Stober method, may be employed to accomplish this step. The silane precursor, TEOS, and FITC Dextran-TRITC-Con, were first prepared in absolute ethanol. The chemical equation for porous silica nanoparticles is shown below;

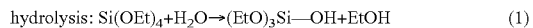
hydrolysis: $Si(OEt)_4 + H_2O \rightarrow (EtO)_3Si\text{—}OH + EtOH$    (1)

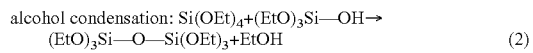
alcohol condensation: $Si(OEt)_4 + (EtO)_3Si\text{—}OH \rightarrow (EtO)_3Si\text{—}O\text{—}Si(OEt)_3 + EtOH$    (2)

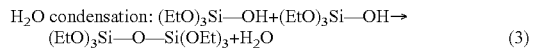
$H_2O$ condensation: $(EtO)_3Si\text{—}OH + (EtO)_3Si\text{—}OH \rightarrow (EtO)_3Si\text{—}O\text{—}Si(OEt)_3 + H_2O$    (3)

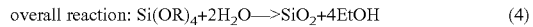
overall reaction: $Si(OR)_4 + 2H_2O \rightarrow SiO_2 + 4EtOH$    (4)

Other fluorophore pairs used in this invention include the organic dyes with the excitation wavelength in visible range, or even the near Infrared region. The method to encapsulate the fluorescent bioassay within porous nanomaterials can be water-in-oil microemulsion, sol-gel method.

The porous zeolite nanomaterials are able to keep multiple fluorophore molecules.

Step (2) involves assembling the dye-loaded nanoparticles on a polydimethylsiloxane (PDMS) slice. To enhance the better adhesion of the silica nanoparticles to the PDMS surface, poly(diallyldimethyl ammonium chloride) (PDAC) and sulfonated polystyrene (SPS) were assembled onto the pre-treated substrate, PDMS. The process of the pre-treated PDMS is described as follows.

Pre-Treatment Procedure

Chemical Preparations:

Deionized water; PDMS (base: curing=10:1), SPS (0.01 M, pH=5), PDAC (0.01 M, pH=6), Fluorescent assay loaded silica nanoparticles (5%), (3-aminopropyl)-triethoxysilane (10%).

Procedures:

Poly(dimethylsiloxane) (PDMS, Sylgard 184 silicone elastomer, Dow Corning) was used to prepare substrates by mixing the base and curing agent in a 10:1 ratio, degassing and spin-coating this mixture on a Si wafer, and curing for 48 h at 80° C.

Deionized water (>18 MXcm, Millipore Milli-Q) was exclusively used in all aqueous solutions and rinsing procedures.

Sulfonated polystyrene (SPS) (sodium form, weight-average molecular weight, Mw=70 000 g mol-1) and poly(diallyldimethyl ammonium chloride) (PDAC) (Mw=200 000 g mol-1).

Sequential adsorption of polyelectrolyte multilayers was performed by using an HMS programmable slide stainer (Zeiss, Inc.), where the dipping time for polymers and nanoparticles was 15 min followed by three rinses in Milli-Q water; one two-minute rinse and two one-minute rinses.

Both the SPS and PDAC solutions (0.01 M based on repeat unit) were adjusted to the dipping pH (5.0 for SPS, 6.0 for PDAC) with HCl or NaOH. The pH of the nanoparticle solutions was usually 9.0.

In a typical experiment, the PDMS substrate was pretreated with an air plasma for 10 s, then quickly immersed into a solution of (3-aminopropyl)-triethoxysilane (10%) for 2 h (to functionalize the surface with positive charges).

Fourteen (14) bilayers of PDAC/SPS were assembled on this PDMS substrate to promote nanoparticle adhesion.

Figure 5:
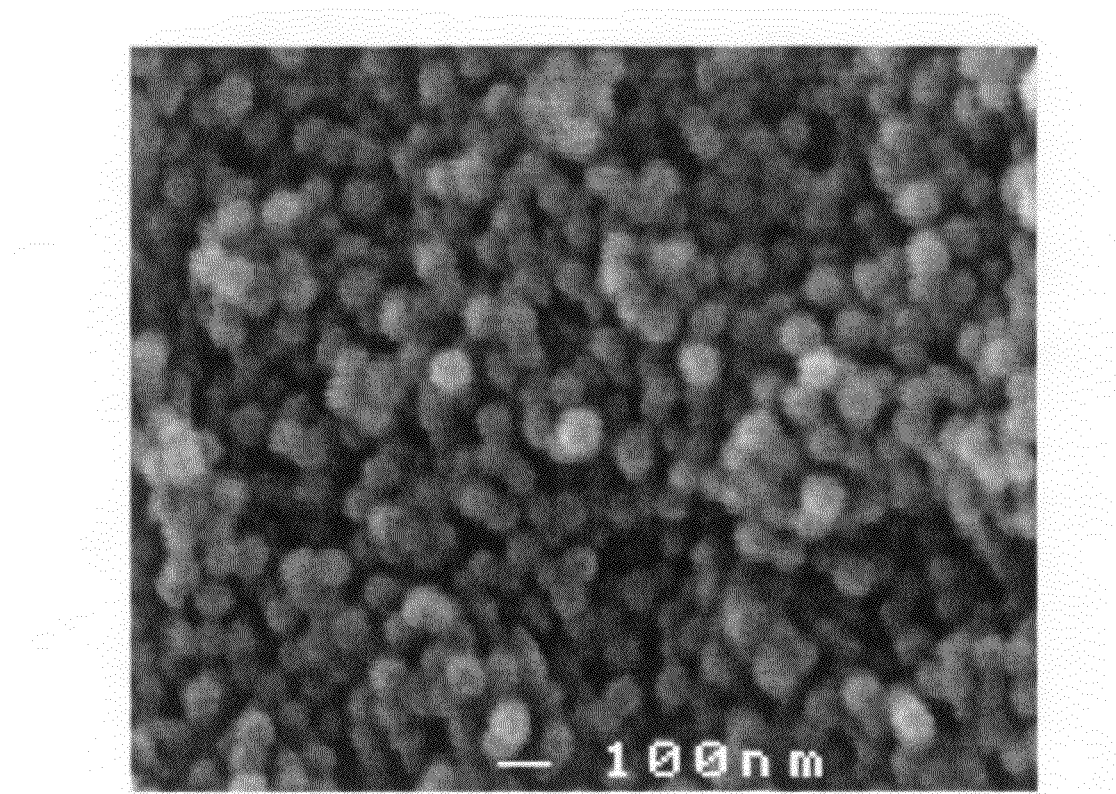
FIG. 5 shows scanning electron micrographs (SEM) of assembling nanoparticles on silicone (PDMS) in which the dimension of the inserted slice (L*W*H) is 1.5 mm*1.5 mm*10 μm as optical probe.

Subsequently, 1-4 bilayers of PDAC/fluorescent assay loaded silica nanoparticles were deposited onto the adhesion layers. SEM microscopy indicates the deposition of one or more PDAC/silica nanoparticle bilayers (~100 nm particles) onto the adhesion-layer-coated PDMS substrates as shown in FIG. 5.

Step (3) involves fabrication of the transducer, e.g. optical probe, or magnetic probe, loaded contact lens. Either one-step or two-step photo-polymerization is applied to integrate the sensor into the contact lens. To one-step photopolymerization, sensor merged in hydrogel solution (200 µl) is cured under a deep-UV processing. To two-step method, first the bottom layer (5-10 µm) of hydrogel, such as p-HEMA, silicone, and other lens materials, is polymerized. Following then, the transducer, optical probe, or magnetic probe, is loaded on the bottom layer, and mixed with the hydrogel solution (100-150 µl) for the second cuing. The total thickness of the lens device is about 20-25 µm. A brief description of photopolymerization of integrating sensor into contact lens is as follows;

Chemical Preparations:

purified HEMA solution;

photo-initiator: ,2-dimethoxy-2-phenyl acetophenone (DMPA);
crosslinker ethylene glycoldiacrylate (EGDA); and
solvent: DMSO
Procedures:
(1) Mixing the chemical solution of HEMA, ohotoinnitiator, and crosslinker with the volume ratio of 500:20:1
(2) Fixing the position of sensor in the contact lens mould.
(3) 1 kW Hg(Xe) Deep UV Source of 220-260 nm wavelengths is used to polymerized the HEMA solution to integrate the sensor into the HEMA contact lens.

Step (4) indicates the color change of the optical probe loaded in contact lens when the tear glucose replaces the dye B to conjugate onto the Con-A in nanostructured optical sensor. To study of the efficacy of optical sensor loaded contact lenses produced herein, studies involves adding glucose solution on the surface of the contact lens were conducted followed by detection of the shift of florescence, i.e. RET analysis.

Figure 4:
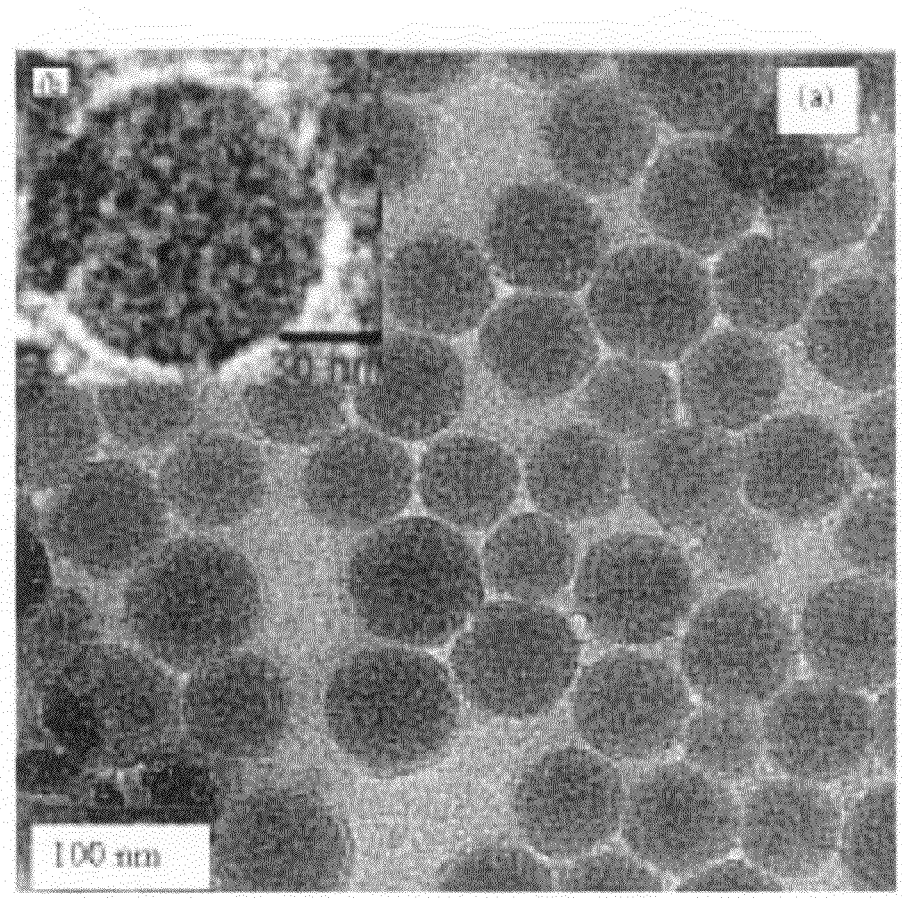
FIG. 4 shows TEM micrograph of porous silica nanoparticles encapsulated FITC Dextran-TRITC-Con produced by modified Stober method, showing that the average diameter of nanoparticles is about 100 nm.

FIG. 4 shows TEM micrograph of porous silica nanoparticles encapsulated FITC Dextran-TRITC-Con produced by the modified Stober method disclosed above, showing that the average diameter of the nanoparticles is about 100 nm. Studies by the inventors demonstrate that the sol-gel and the water-in-oil microemultion are also the good method to load the fluorescent assays in the silica nanoparticles.

FIG. 5 shows scanning electron micrographs (SEM) of assembling nanoparticles on PDMS in which the dimension of the inserted slice (L*W*H) is 1.5 mm*1.5 mm*10 µm as optical probe.

Figure 6:
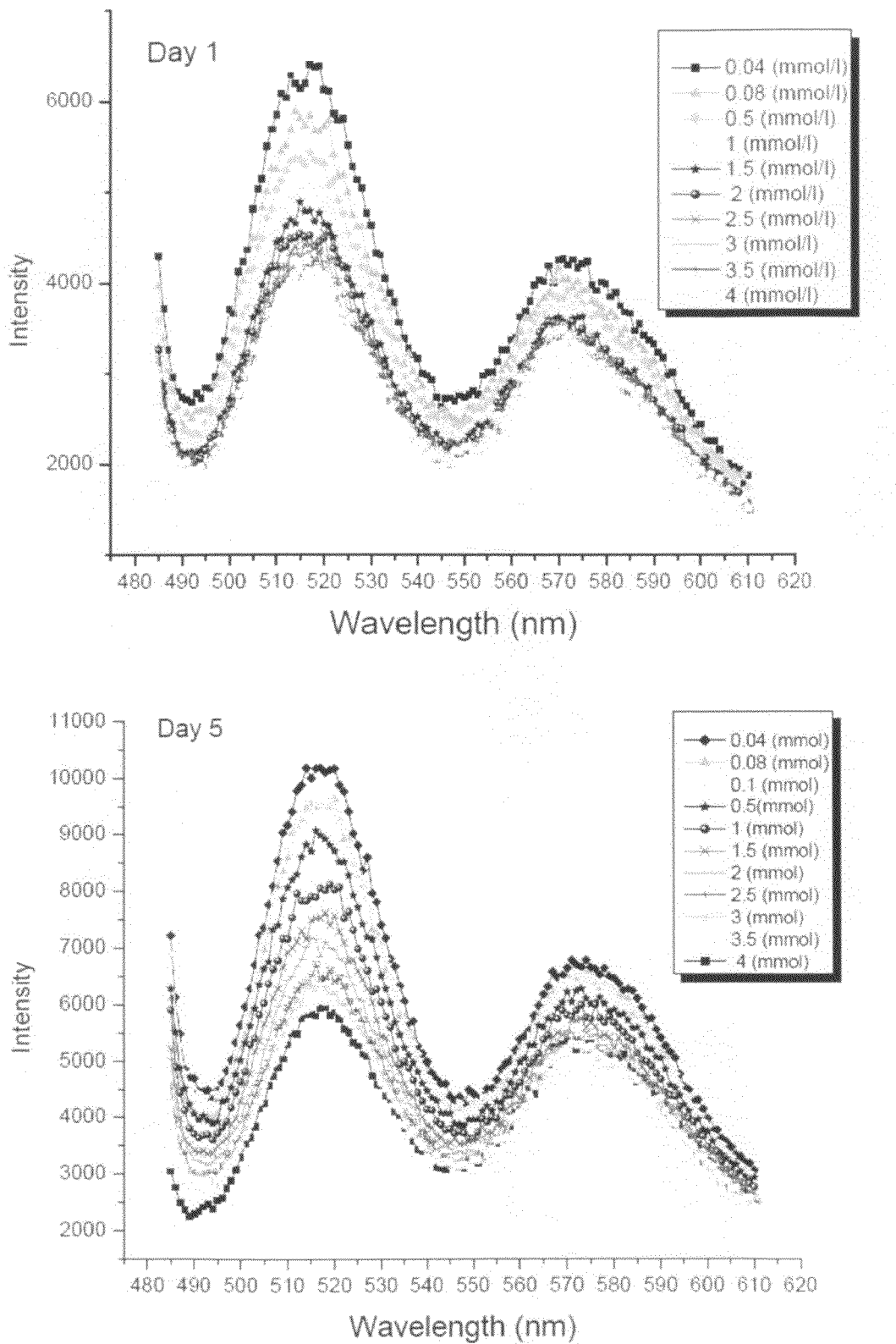
FIG. 6 shows the florescent shifts of the nanostructured optical sensor as the function of the concentration of glucose. The results indicate that there is at least 65 nm shifts from 510 nm to 575 nm in the visible range. The sensor is able to detect the change of concentration from 0.04 mM to 4 mM. The results show that the intensity of the signal of FITC is decreased with the increase of the concentration of glucose. This demonstrates that the color change can be visually detected when the concentration of glucose is larger than 3 mM. Furthermore, the device is able to continuously detect the change for 5 days.

FIG. 6 shows the florescent shifts of the nanostructured optical sensor as the function of the concentration of glucose. The results indicate that there is at least 65 nm shifts from 510 nm to 575 nm in the visible range. The sensor is able to detect the change of concentration from 0.04 mM to 4 mM. The results show that the intensity of the signal of FITC-dextran is decreased with the increase of the concentration of glucose. This demonstrates that the color change can be visually detected when the concentration of glucose is larger than 3 mM. Furthermore, the device is able to continuously detect the change for 5 days.

Figure 7:
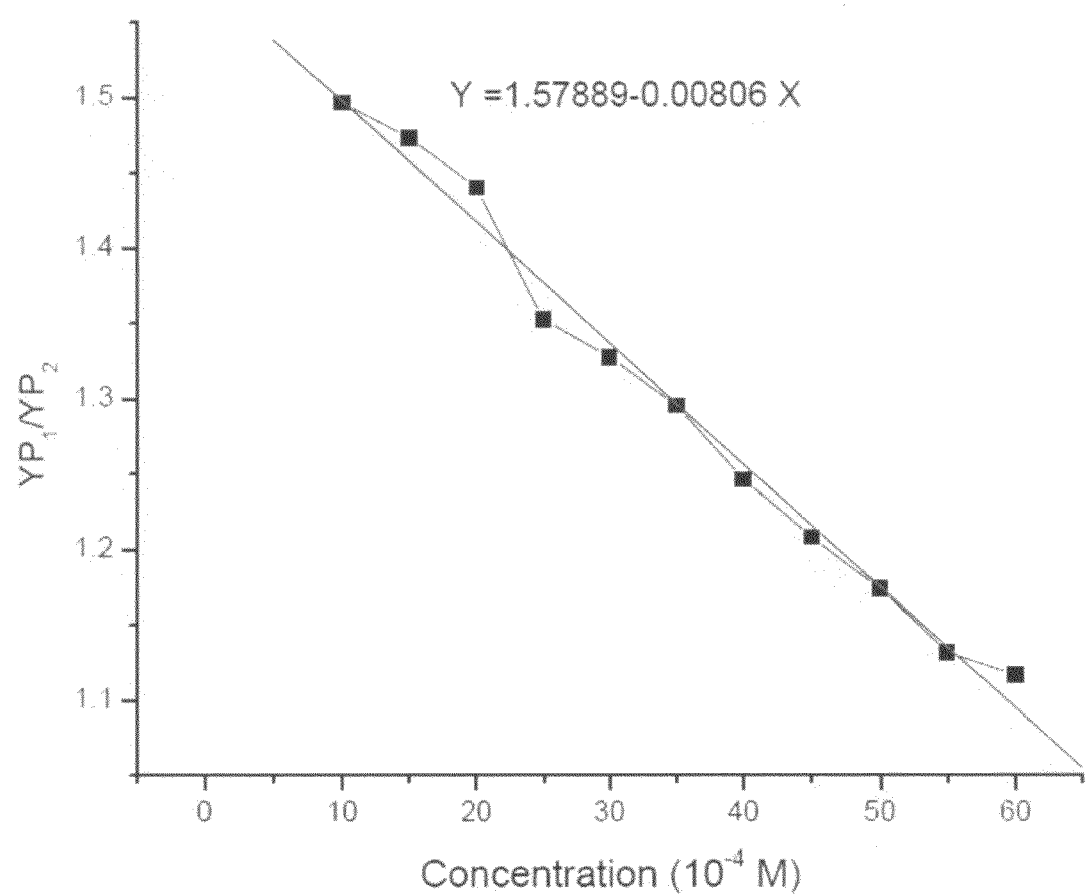
FIG. 7 shows the relationship of the fluorescent module and the concentration. It indicates the optical device is able to detect achieves sensitivity in the range of 0-6.5 mM (~0-1200 mg/dL).

FIG. 7 shows the relationship of the fluorescent module and the concentration. It indicates the optical device is able to detect achieves sensitivity in the range of 0-6.5 mM (~0-1200 mg/dL).

Figure 8:
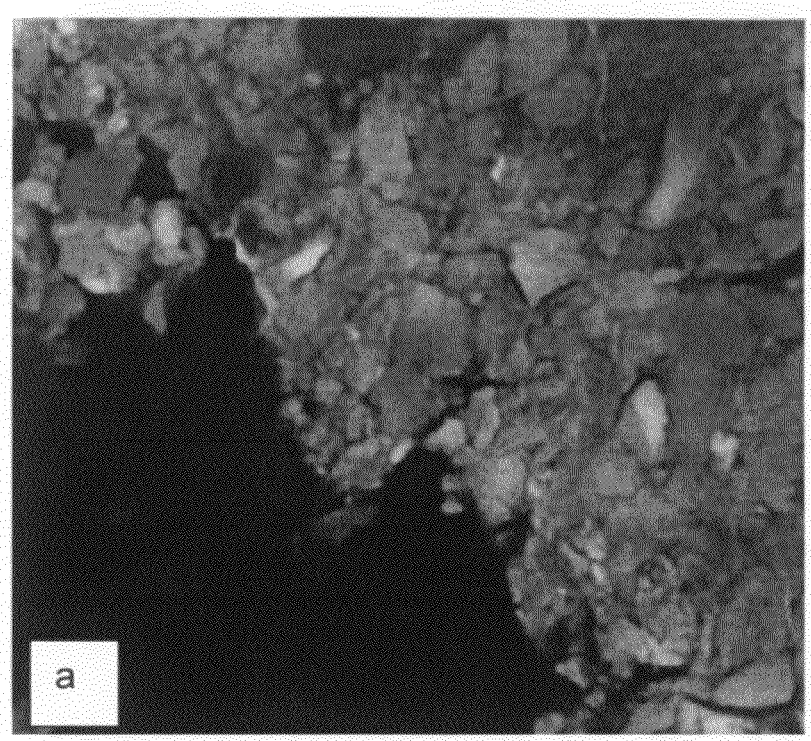
FIG. 8 shows the confocal laser microscopy images before adding glucose and after adding glucose (0.1 mM). The responsive period is less than 5 min. The result indicates the device can be able to fast detect the change of the glucose when the concentration increased from 0 to 0.1 mM.
Figure 8:
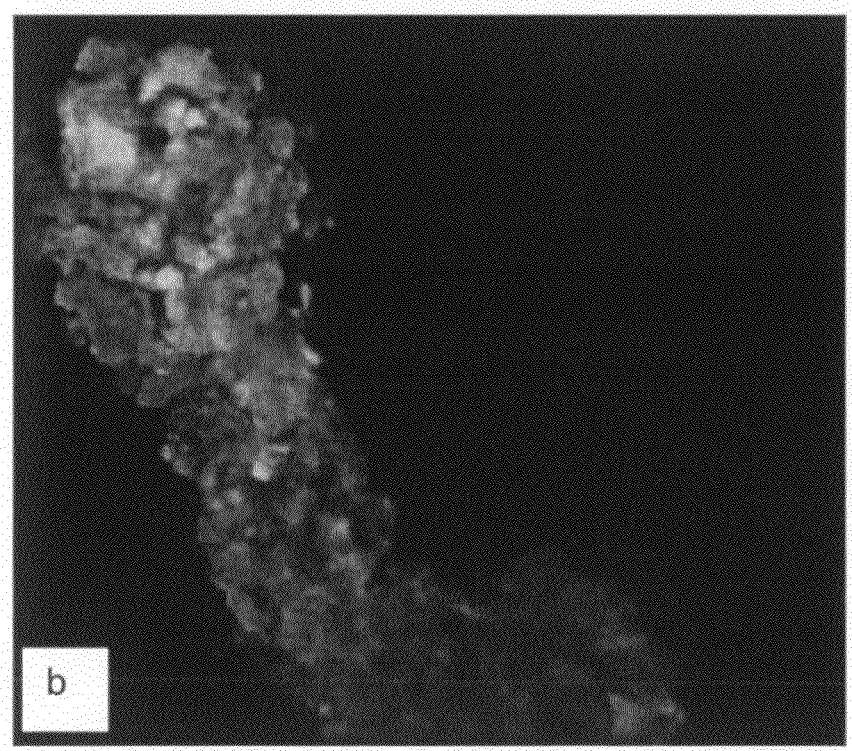

FIG. 8 shows confocal laser microscopy images before adding glucose and after adding glucose (0.1 mM). The responsive period is less than 5 min. The result indicates the device can be able to fast detect the change of the glucose when the concentration increased from 0 to 0.1 mM.

The fluorophore 1 (organic dye A), TRITC-dextran is red color, and fluorophore 2 (organic dye B), FITC-dextran, is green in the florescent microscopy.

Fabrication of contact lens loaded with the biosensor is then performed. Different hydrogel materials may be used including HEMA, PDMS, and collagen. The fabrication methods may utilize photo-crosslinking polymerization and thermo-crosslinking polymerization and in-situ polymerization. The optical transmission of silica nanoparticles loaded in p-HEMA was studied. The results indicated that the light transmission is equal to about 80% of pure p HEMA when the loading rate of silica nanoparticles is over 0.5 µg per 20 µl lens materials.

Detection of the color change of the portion of the contact lens containing the biosensor for glucose can be visually detected when the concentration of glucose is larger than 3 mM. The device can achieve sensitivities in the range of greater than 0 to 1800 mg/dL of glucose The best reported Con-A/dextran systems for sensing glucose based on competitive binding and RET had the sensitivity in the range of $\sim 10^{-4}$ ratio units/(mg/dL) [18] and shows Increasing fluorescence with increasing glucose concentration. The fluorescence intensity is displayed digitally on the hand-held photofluorometer and may also be sent by telemetry to an insulin pump.

While the invention has been illustrated using the organic dye FITC Dextran-TRITC-Con, it will be appreciated that others may be used as well. Specifically, the conjugation of Con A, a enzyme (protein), and glucose has been proved. Thus, the form of assay can be (a) single fluorophor-protein (Con A). For a single fluorophor assay, it may include either of tetramethyl rhodamine isothiocyanate (TRITC), or 9,10-diphenyl anthracene. The binding between Con A and glucose will affect the intensity of the single fluorophor.

Another organic dye that may be incorporated into contact lenses include Fluorophor 1-Protein (Con A)-Fluorophor 2. This is a more accurate assay for measuring the concentration of glucose using tear samples. Once the glucose conjugates to the enzyme (Con A), the change is measured and evaluated by the dependence of both of florescent intensity (I) and wavelength ($\lambda$) as the function of the concentration of glucose. This double method of using both the florescent intensity (I) and wavelength ($\lambda$) is more accurate because it evaluates the effect of the concentration of glucose on two relative parameters, i.e. the two ratios of florescent intensity (I) and wavelength ($\lambda$) to Fluorophor 1 and Fluorophor 2. It requires that the two fluorophors have at least 30 nm difference in florescent wavelength. The fluorophor pair can be any one of, but are not limited to, rhodamine and fluorescein isothiocyanate (FITC), tetramethyl rhodamine isothiocyanate (TRITC), and fluorescein isothiocyanate (FITC), or tetramethylrhodamine (TAMRA) and FITC (FITC-dextran).

Similarly, while PDMS was used as the substantially clear substrate, it will be appreciated by those skilled in the art that other transparent and high-oxygen-permeable materials may be used, including, but not limited to, silicone acrylates and silicone derivatives, such as polymethylmethacrylate (PMMA), polydimethylsiloxane, and fluoroether.

In addition to silica nanoparticles other highly porous nanostructures may be used, including transparent bio-inorganic materials, nanotubes, nanofilms, and bio-polymer nanostructures, such as alginate, chitosan nanoparticles (NP), nanofibers, or 2-D, 3-D foams with highly nanoporous structures.

In the present invention, employing the physio-chemical interaction between porous nanoparticles and dye A helps to keep the protein to remain in the contact lens and allows for the continuous detection of the analytes of interest over extended periods of times, such as a week, due to the nanostructures encapsulated in the silicone hydrogel.

A major reason for the success of the contact lens with the integrated biosensor disclosed herein is that the porous structures of the nanoparticles act as an analyte (e.g. tears, glucose) collector, sucking up moisture, and therefore assists in the achievement of high concentrations of analyte due to the large surface area to volume ratio and inter-porous structures of the nanoparticles.

The contact lenses disclosed herein may also be configured to diminish the discomfort of dry eyes which is a key challenge to contact lens, To minimize the symptoms of dry eyes, the contact lenses may incorporate nano/micro spheres containing artificial tears so that when being worn, the release of the artificial tears from the nano/microspheres occurs and delivers the artificial tears to the eyes through the contact lens.

FIG. 9 shows the contact lens is able to load micro/nanospheres to deliver artificial tears or other payload to diminish the symptoms of dry eyes.

FIG. 10 displays the porous hydrogels len materials, e.g. p(HEMA), which has high oxygen permeability to help minimize the symptoms of dry eyes. Meanwhile, the porous structure helps the laden sensor absorb tear sample.

FIG. 11 shows releasing profiles of artificial tears through the micro/nano sphere-loaded contact lens sensor.

The contact lens integrated with a biosensor is also developed to be able to deliver artificial tears through the loaded transparent micro/nano-spheres as shown in FIG. 9. The release kinetics of artificial tears through the alginate sub-microspheres loaded in HEMA is shown in the FIG. 10. These results show that the tear release profile is able to last over two days.

Another strategy is to decrease the temperature of the contact lens. Martin and Fatt [19] have shown that there is a slight increase in temperature beneath the lens. Thus, decreasing the temperature beneath the lens is able to minimize the discomfort caused by dry eyes. There are several research has been conducted. For instance, studies shows that the antipsychotic drug (APDs) are able to decrease core body temperature, which is correlated to the corneal surface temperature [20].

The present invention provides a contact lens integrated with a biosensor for non-invasive sensing of optical actives of tear glucose. In summary, new glucose-sensing contact lenses have been developed by doping strategically useful optical nanocomposite probes into commercially available contact lenses. The probes are completely compatible with the contact lense material and can readily detect glucose changes of up to several millimolar, appropriate for the tear glucose concentration range of diabetics (i.e. 0.5-5 mM). The contact lenses have a 90% response time of about 5 min, allowing the continuous and noninvasive monitoring of ocular glucose. This is a significant improvement over enzymatic methods based on blood sampling by finger pricking, with many diabetics currently begrudgingly testing between four and six times daily.

While the present invention has disclosed a combined biosensor/contact lens for monitoring of glucose levels, it will be appreciated that the biosensor may be configured to detect other bioanalytes in addition to glucose, including but not limited to other physiological analytes in tear, such as $Na^+$, $K^+$, $Ca^{2+}$, $Mg^{2+}$, histamine, urea, lactate and cholesterol, which could also be monitored in the near future through similar intelligent contact lens based sensing platforms. In this regard, new contact lenses for the determination of multiple tear analytes, such as lactate, sodium and potassium, might be realized, and could even be developed for monitoring the core temperature and pressure using multiple transduction agents in multiple sensor spots.

The porous nanostructures are able to store multiple dyes and materials to the same sensing medium, allowing synergistic sensing schemes for the detection of more types of analytes, based on ion correlation or enzyme reaction. Malachite green (MG) and crystal violet (CV) are able to detect $Na^+$ and $K^+$. Diaza-18-crown-6 appended with two 5-chloro-8-hydroxyquinolin-7-yl groups (1) serves as an effective chemosensor for Mg2+. Bichromophoric podand systems serve as sensors for $Ca^{2+}$ and histamine. Also, some of pH-sensitive fluorophore, e.g. 8-hydroxypyrene 1,3,6-trisulfonic acid (HPTS or pyranine), immobilized in inorganic zeolite nanostructures, wherein the fluorophore is protonated, are able to react with ammonia.

A significant advantage of the present invention is that it provides a disposable, optical sensing, and noninvasive glucose biosensor formed with nanostructure-loaded contact lens. The present biosensor uses a cost effective optical transducer and exhibits superior behavior to previous biosensor based contact lens based on the boronic acid/glucose and glucose-binding protein/glucose interactions. The present invention uses nanoparticles to protect the florophores from leaching. Furthermore, the biosensor loaded contact lens disclosed herein employs dye A-protein-dye B to act as the optical probe. An advantage of this approach is that the concentration of glucose is detected as a function of both resonance energy transfer and the intensity of the florescent signal. The stronger binding (physio-chemical interaction) between nanoparticles and florophore A-protein-glucose helps in the release of protein B.

In addition, this invention takes efforts to diminish the discomfort caused by dry eyes which is a common issue to ware a contact lens. Some methods are related to the delivery of artificial tears and development of the high oxygen permeable hydrogel lens matrix. It is noted that the transducer and the signal measure system is able to adjust in according to the dynamic change of the concentration of tear films.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1 detectable constituents in tears for the diagnosis of the related disease

| Detectable constituents in tear through the invited device | Normal concentration in Tear | Disease caused by the abnormal concentration of the detectable constituents |
|---|---|---|
| Glucose | 0.4 mM | diabetics |
| Urea | Similar to the blood values of urea nitrogen | Urea cycle defects |
| Ketone | <5 mg % | Diabetic keto acidosis (DKA) |
| Potassium | 15-30 milliequivalents (mEq) | Potassium disordered (range from hyperkalemia to hypokalemia) |
| Calcium | 0.4-0.8 mM | Neuromuscular irritability |
| Magnesium | 0.5-1.1 mM | Neuromuscular irritability |
| virus | N/A | HIV |

REFERENCES

[1]. K. B. Bjerrum, J. U. Prause, Graefe's Arch Clin Exp Opthalmol (1994) 232:402-405.
[2] http://en.wikipedia.org/wiki/Biosensor.
[3] D. C. Robbins, in "Diabetes Clinical Science in Practice", Edited by R. D. G. Leslie St Bartholomew's Hospital, London.
[4] W. F. March, F. E. Smith, P. Herbrechtsmeier, A. Domschke, C. Morris, *Diabetes* 50, A125 (2001).

[5] D. Meadows, J. S. Schultz, *Talanta* 35, 145 (1988):
[6] K. Mitsubayashi, M. Suzuki, E. Tamiya, I. Karube, *Anal. Chim. Acta* 289, 27 (1994).
[7] T. R. Stolwijk, J. A. van Best, H. P. J. Lemkes, R. J. W. Keizer, J. A. Oosterhuis, *Int. Opthalmol.* 15, 377 (1991).
[8] L. Tolosa, I. Gryczynski, L. R. Eichorn, J. D. Dattelbaum, F. N. Castellano, G. Rao, J. R. Lakowicz, *Anal. Biochem.* 267, 114 (1999).
[9] L. Tolosa, H. Malak, G. Rao, J. R. Lakowicz, *Sens. Actuators, B* 45, 93 (1997).
[10] S. D'Auria, N. Dicesare, Z. Gryczynski, I. Gryczynski, M. Rossi, J. R. Lakowicz, *Biochem. Biophys. Res. Commun.* 274, 727 (2000).
[11] P. R. Chatterjee, S. De, H. Datta, S. Chatterjee, M. C. Biswas, K. Sarkar, L. K. Mandal, *J. Ind. Med. Assoc.,* 101, 481 (2003).
[12] F. E. Cappuccio, J T. Suri, D. B. Cordes, R. A. Wessling R. A, B. Singaram, *J Fluores,* 14, 521 (2004).
[13] E. A. Moschou, B. V. Sharma, K. S. Deo, S. Daunert, *J Fluores,* 14, 535 (2004).
[14] M. D. Philips and T. D. James, *J Fluores,* 14, 549 (2004).
[15] M. Schaferling, M. Wu, and O, S. Wolfbeis, *J Fluores,* 14, 561, (2004).
[16] S. Chinnayelka and M. J. McShane, *J Fluores,* 14, 585 (2004).
[17] S. A. Grant, J. Xu, E. Bergeron, and J. Mroz, *Biosens. Bioelectron.* 16, 231 (2001).
[18] D. L. Meadows and J. S. Schultz. *Anal. Chim. Acta,* 280, 21 (1993).
[19] D. Martin and I, Fatt, *Acta Opthalmologica (Copenhagen),* 64, 512-518 (1986).
[20] R. Shiloh, L. Bodinger, N. Katz, M. Sigler, R. Stryjer, H. Hermesh, H. Munitz, A. Weizman, *Neuropsychobiology,* 48, 1-4, (2003)

Therefore what is claimed is:

1. A contact lens with integrated biosensor, comprising:
   a) a contact lens having incorporated therein a biosensor for sensing bioanalytes present in tears;
   b) the biosensor including a physiologically compatible oxygen permeable substantially transparent and flexible substrate, and physiologically compatible porous nanostructures adhered on said physiologically compatible oxygen permeable and flexible substrate, a physiologically compatible fluorescent assay containing at least one physiologically compatible fluorescent dye encapsulated in said physiologically compatible porous nanostructures,
   said physiologically compatible fluorescent dye being selected to react or bind with a selected bioanalyte present in tears such that reacting or binding of the bioanalyte with the physiologically compatible fluorescent dye is responsively accompanied by a detectable change in optical properties of the physiologically compatible fluorescent dye indicative of the presence of the bioanalyte in tears when the contact lenses with integrated biosensor is on a person's eye and said physiologically compatible porous nanostructures having a porosity selected for collecting the tears; and
   c) said biosensor being located in said contact lens at a position off centre in the contact lens such as to not directly obstruct the vision of the person wearing the contact lens.

2. The contact lens with integrated biosensor according to claim 1 wherein said physiologically compatible porous nanostructures are zeolite materials having high surface areas.

3. The contact lens with integrated biosensor according to claim 2 wherein said zeolite materials are aluminosilicate nanocomposite zeolites.

4. The contact lens with integrated biosensor according to claim 1 wherein said physiologically compatible porous nanostructures are silica nanoparticles.

5. The contact lens with integrated biosensor according to claim 1 wherein said physiologically compatible porous nanostructures are selected from the group consisting of silica nanoparticles, nanotubes, nanofilms, and bio-polymer nanostructures including alginate, chitosan nanoparticles (NP), nanofibers, 2-D and 3-D foams with highly nanoprorous structures.

6. The contact lens with integrated biosensor according to claim 1 wherein said physiologically compatible oxygen permeable substantially transparent and flexible substrate is PDMS.

7. The contact lens with integrated biosensor according to claim 1 wherein said physiologically compatible oxygen permeable and substantially transparent substrate is selected from the group consisting of silicone acrylates, silicone derivatives, polyacrylates, and fluorofoether, and the polyacrylates are selected from the group consisting of polymethylmethacrylate (PMMA) and polydimethylsiloxane.

8. The contact lens with integrated biosensor according to claim 1 wherein said detectable change in optical properties of the physiologically compatible fluorescent dye is a color change of that portion of the contact lens into which the biosensor is incorporated, which color change is readily detectable by the person wearing the contact lens.

9. The contact lens with integrated biosensor according to claim 1 wherein said physiologically compatible fluorescent dye is FITC Dextran-TRITC-Con A, and wherein the bioanalyte being detected for is glucose present in tears.

10. The contact lens with integrated biosensor according to claim 1 wherein said physiologically compatible fluorescent dye is selected from the group consisting of FITC Dextran-TRITC-Con A, tetramethyl rhodamine isothiocyanate (TRITC) and 9,10-diphenyl anthracene, and wherein the bioanalyte being detected for is glucose present in tears and the presence of the glucose is detected by fluorescent resonant energy transfer (FRET) efficiency.

11. The contact lens with integrated biosensor according to claim 1 wherein said physiologically compatible fluorescent dye is a pair of Fluorophor 1- Protein (Con A)- Fluorophor2, and wherein Fluorophor 1 and Fluorophor 2 have at least 30 nm difference in florescent wavelength.

12. The contact lens with integrated biosensor according to claim 11 wherein the pair of Fluorophor 1 and Fluorophor 2 include rhodamine and fluorescein isothiocyanate (FITC), tetramethyl rhodamine isothiocyanate (TRITC), and fluorescein isothiocyanate (FITC), or tetramethylrhodamine (TAMRA) and FITC (FITC-dextran).

13. The contact lens with integrated biosensor according to claim 1 wherein the porous nanostructures are configured for storing multiple physiologically compatible fluorescent assays, and the bioanalytes being detected for are $Na^+$ and $K^+$ present in tears.

14. The contact lens with integrated biosensor according to claim 13 wherein said physiologically compatible fluorescent assays are malachite green (MG) and crystal violet (CV).

15. The contact lens with integrated biosensor according to claim 1 wherein said physiologically compatible fluorescent dye is diaza-18-crown-6 appended with two 5-chloro-8-hydroxyquinolin-7yl groups, and wherein the bioanalyte being detected for is $Mg^{2+}$ present in tears.

16. The contact lens with integrated biosensor according to claim 1 wherein said physiologically compatible fluorescent dye 8-hydroxypyrene 1,3,6-trisulfonic acid, and wherein the bioanalyte being detected for is ammonia present in tears.

17. The contact lens with integrated biosensor according to claim 1 wherein said biosensor includes transparent micro/nanospheres having a diameter in a range from about 20 nm to about 200 nm, said transparent micro/nanospheres containing any one or combination of drugs, artificial tears, and cooling agents to reduce symptoms of dry eyes.

18. The contact lens with integrated biosensor according to claim 17 wherein said cooling agents include antipsychotic drugs.

19. The contact lens with integrated biosensor according to claim 17 wherein said artificial tears include solutions of carboxymethyl cellulose, hydroxypropyl methylcellulose, hypromellose, and hydroxypropyl cellulose.

20. The contact lens with integrated biosensor according to claim 17 wherein said transparent micro/nanospheres are made from materials selected from the group consisting are PLGA, collagen, hydrogels, and alginate.

21. The contact lens with integrated biosensor according to claim 1 wherein said physiologically compatible porous nanostructures having the selected porosity contain one or more fluorescent molecules for the detection of different tear components, and acts as a reservoir to collect enough amount of tear samples in a short period to decrease a sensor response time and increase the sensitivity of sensor.

22. The contact lens with integrated biosensor according to claim 1 wherein said biosensor includes porous structures embedded therein having a size and porosity to allow update of sample tears by the porous structures and patterned tunnels.

23. The contact lens with integrated biosensor according to claim 22 wherein said porous structures are selected from the group consisting of mesoporous silica nanomaterial, hollow tubes having nano/micro-scale dimensions, fibers having nano/micro-scale dimensions, and porous polymer spheres having nano/microscale dimensions.

* * * * *

UNITED STATES PATENT AND TRADEMARK OFFICE
CERTIFICATE OF CORRECTION

PATENT NO. : 8,385,998 B2
APPLICATION NO. : 12/588733
DATED : February 26, 2013
INVENTOR(S) : Zhang et al.

It is certified that error appears in the above-identified patent and that said Letters Patent is hereby corrected as shown below:

In the Claims

Col. 15, lines 1-4 in Claim 16 of the Letter Patent, the word "is" should appear between 'dye' and '8-hydroxypyrene', such that Claim 16 should correctly read:

16. The contact lens with integrated biosensor according to claim 1 wherein said physiologically compatible fluorescent dye is 8-hydroxypyrene 1,3,6-trisulfonic acid, and wherein the bioanalyte being detected for is ammonia present in tears.

Signed and Sealed this
Nineteenth Day of November, 2013

Teresa Stanek Rea
*Deputy Director of the United States Patent and Trademark Office*